United States Patent [19]

Bayerl et al.

[11] Patent Number: 4,582,647
[45] Date of Patent: Apr. 15, 1986

[54] PROCESS FOR THE PREPARATION OF PURE 2,6-DICHLOROBENZONITRILE

[75] Inventors: Herbert Bayerl, Trostberg; Walter Pollwein, Mühldorf, both of Fed. Rep. of Germany

[73] Assignee: SKW Trostberg Aktiengesellschaft, Trostberg, Fed. Rep. of Germany

[21] Appl. No.: 718,851

[22] Filed: Apr. 2, 1985

[30] Foreign Application Priority Data

Apr. 6, 1984 [DE] Fed. Rep. of Germany ....... 3412937

[51] Int. Cl.$^4$ ........................................... C07C 120/14
[52] U.S. Cl. .................................................. 558/327
[58] Field of Search ....................... 260/465 C, 465 G

[56] References Cited

U.S. PATENT DOCUMENTS

| 2,828,325 | 3/1958 | Hardy | 260/465 C |
| 3,732,275 | 5/1973 | Platz et al. | 260/465 C |
| 4,124,631 | 11/1978 | Hayami et al. | 260/465 C |

FOREIGN PATENT DOCUMENTS 947167 1/1964 United Kingdom .

*Primary Examiner*—Dolph H. Torrence
*Attorney, Agent, or Firm*—Felfe & Lynch

[57] ABSTRACT

The present invention provides a process for the preparation of pure 2,6-dichlorobenzonitrile by the ammonoxidation of 2,6-dichlorotoluene in the presence of a catalyst based on vanadium-molybdenum oxide, wherein the reaction is carried out in a fluidized bed process and water is sprayed into the reaction gases after leaving the fluidized bed reactor.

12 Claims, No Drawings

PROCESS FOR THE PREPARATION OF PURE 2,6-DICHLOROBENZONITRILE

The present invention is concerned with a process for the preparation of pure 2,6-dichlorobenzonitrile by the ammonoxidation of 2,6-dichlorotoluene.

2,6-Dichlorobenzonitrile is of great technical importance because of its good herbicidal action (cf. H. Wegler "Chemie der Pflanzenschutz- und Schadlingsbekämpfungsmittel", Vol. 5, pp. 229–230, pub. SpringerVerlag, 1977).

The preparation of this compound is relatively complicated since it is only accessible via multistage reactions.

Thus, for example, Federal Republic of Germany Patent Specification No. 12 06 422 describes a process for the preparation of 2,6-dichlorobenzonitrile in which 6-chloro-2-nitrotoluene is reacted with chlorine in the presence of a heterocyclic tertiary amine. Quite apart from the fact that the starting material, 6-chloro-2-nitrotoluene, is very difficult to obtain, this process suffers from very serious disadvantages with regard to yield and purity. Thus, 2,6-dichlorobenzonitrile is only obtained as a by-product which has to be separated from the main product, 2,6-dichlorobenzal chloride, as well as from 2,6-dichlorobenzyl chloride. Consequently, it is understandable why the purification makes necessary very high investment and operational costs when it is desired to obtain a product which is in any way to be considered as being useful.

From Federal Republic of Germany Patent Specification No. 11 16 209 there is also known, inter alia, a process for the preparation of 2,6-dichlorobenzonitrile in which this product is obtained by ammonoxidation of 2,6-dichlorotoluene in a fixed bed process in yields of from 27 to 62%. Besides these only modest yields, a further disadvantage of this process is that the purification of the desired product takes place by distillation or crystallisation from solvents, which makes the process relatively laborious.

Therefore, the problem with which the present invention is concerned is to provide a process for the preparation of pure 2,6-dichlorobenzonitrile by the ammonoxidation of 2,6-dichlorotoluene in the presence of a catalyst based upon vanadium-molybdenum oxide which does not display the above-mentioned disadvantages of the prior art but makes it possible, without special working up and purification steps, to obtain a very pure product in good yields. A relatively impure starting material is thereby also possibly to be used.

Thus, according to the present invention, there is provided a process for the preparation of pure 2,6-dichlorobenzonitrile by the ammonoxidation of 2,6-dichlorotoluene in the presence of a catalyst based on vanadium-molybdenum oxide, wherein the reaction is carried out in a fluidised bed process and water is sprayed into the reaction gases after leaving the fluidised bed reactor.

Thus, we have, surprisingly, found that, in this manner, very pure 2,6-dichlorobenzonitrile is obtained so that a further purification step, such as distillation or recrystallisation, is no longer necessary. Furthermore, the product is obtained in an especially finely-divided form, which is also advantageous for certain uses.

In the case of the process according to the present invention, as is usual in the case of ammonoxidation processes, a gas mixture of 2,6-dichlorotoluene, ammonia and air, which is diluted with nitrogen, is passed through a fluidised bed of the catalyst. The catalyst is preferably vanadiummolybdenum oxide on an aluminium oxide carrier, such as is produced, for example, in the manner described in Federal Republic of Germany Patent Specification No. 10 63 144.

After leaving the reactor, according to the process of the present invention, water is sprayed into the reaction gases, an optimum separation of the product from its impurities thereby being achieved. This measure is decisive for the success of the present invention.

The amount of water sprayed in should preferably be such that the reaction gases are hereby quenched to a temperature of from 20° to 40° C., which, in the case of conventional cooling water temperatures, corresponds to an amount of from 10 to 50 and preferably of from 20 to 30 liters of water per 100 ml. 2,6-dichlorotoluene. Larger amounts of water can also be sprayed into the gaseous reaction mixture but this does not result in any noteworthy further improvement of the product quality, such as purity and particle size. If less than 10 liters of water are used per 100 ml. 2,6-dichlorotoluene, then there is obtained a somewhat more coarsely grained but still readily usable product because the quenching effect is not so strongly marked.

The water can be sprayed in by means of processes and devices which are conventionally employed. Due to the spraying in of the water, the separation of the 2,6-dichlorobenzonitrile as a finely divided solid material is achieved, the impurities, for example ammonium chloride or ammonium carbonate, thereby remaining in the aqueous phase. The 2,6-dichlorobenzonitrile, which is obtained with a purity of 98%, can be discharged together with the water and can be readily separated therefrom by filtration or centrifuging without a further purification step being necessary. If necessary, the product can be dried by conventional methods.

The process according to the present invention is also outstandingly suitable for a continuous carrying out, in the case of which the water is passed in circulation. After separation of the reaction product, the water can hereby again be brought to the necessary cooling temperature by means of heat exchangers and subsequently, after making up for possible losses, can again be spayed into the reaction gases. Depending upon the period of reaction of the process, it is recommended to replace a part of the used water by fresh water in order thus to achieve a product quality which is as constant as possible.

The mole ratio of 2,6-dichlorotoluene to ammonia is preferably 1:2 to 5 and more preferably 1:2.5 to 4, whereas a mole ratio of 2,6-dichlorotoluene to oxygen of 1:3 to 5 has proved to be especially advantageous. However, it is also possible to use a mole ratio outside of this range.

In the case of the ammonoxidation, the reaction temperature is, as far as possible, to be from 400° to 500° C. In the case of going substantially below this temperature range, the proportion of impurities increases, whereas above 500° C., decomposition takes place to an increasing extent so that the yield is considerably reduced.

The contact time of the 2,6-dichlorotoluene with the catalyst is, depending upon the height of the fluidised layer and upon the velocity, preferably from 0.5 to 1 second.

The process according to the present invention is especially characterised by its low technical expense and the low operational and investment costs resulting therefrom, as well as by the high degree of purity of the end product and the possibility of objectively controlling the particle size of the product. A further advantage of the process according to the present invention is that it is not absolutely necessary to start from very pure 2,6-dichlorotoluene. Instead thereof, it is also possible to use impure starting material without this having a marked effect on the purity of the end product.

The following Examples are given for the purpose of illustrating the present invention:

EXAMPLES

The following Examples 1 to 9 are carried out in the following manner:

A gas mixture of 2,6-dichlorotoluene, ammonia and air is passed, with nitrogen, in the stated amount ratios (01 = operational liter referred to 400° C. and atmospheric pressure), through the fluidised bed of catalyst. The catalyst consists of an aluminium oxide carrier with 17% by weight of vanadium oxide and 7% by weight of molybdenum oxide. After an average residence time of 0.7 to 0.8 seconds, the reaction gases leave the reactor with a temperature of about 400° C. Water is sprayed in the given amounts into this reaction mixture and the mixture is cooled to a temperature of from 24° to 28° C. The 2,6-dichlorobenzonitrile thereby separates out in very finely divided form and is removed with the water. After separation of the product by centrifuging, the water is cooled in a heat exchanger and again used for the gas cooling by means of a pump. The given amounts of fresh water are added to the recycled water so that the losses are compensated for and a part of the water circulation is exchanged.

In the case of Examples 1 to 7, an impure 2,6-dichlorotoluene is used which contains 1.7% by weight of organic impurities and 0.2% by weight of water and is dark brown coloured, whereas in the case of Examples 8 and 9 there is used a very pure 2,6-dichlorotoluene containing 0.1% by weight of water and 0.1% by weight of other impurities.

EXAMPLE 1

Starting materials 2,6-dichlorotoluene (DCT)—200 ml./hr.
ammonia ($NH_3$)—158 01/h.
air ($O_2$)—940 01/h.
nitrogen ($N_2$)—3330 01/h.

Mole ratio

DCT:$NH_2$:$O_2$ = 1:4:5
water circulation—40 liters/h.
fresh water—100 ml./h.
waste water—150 ml./h.
Yield: 60%

Product purity (after drying)

2,6-dichlorobenzonitrile—99.7%
2,6-dichlorotoluene—0.1%
water—0.1%
other impurities—0.1%

EXAMPLE 2

Starting materials 2,6-dichlorotoluene—200 ml./h.
ammonia—119 01/h.
air—752 01/h.
nitrogen—3519 01/h.

Mole ratio

DCT:$NH_3$:$O_2$ = 1:3:4
Water circulation, fresh and waste water as in Example 1.
Yield: 63%.

Product purity 2,6-dichlorobenzonitrile—99.3%
2,6-dichlorotoluene—0.1%
water—0.1%
other impurities—0.5%

EXAMPLE 3

Starting materials 2,6-dichlorotoluene—200 ml/h.
ammonia—79 01/h.
air—564 01/h.
nitrogen—3729 01/h.

Mole ratio

DCT:$NH_3$:$O_2$ = 1:2:3
Water circulation, fresh and waste water as in Example 1.
Yield: 70%

Product purity 2,6-dichlorobenzonitrile—98.2%
2,6-dichlorotoluene—0.3%
water—0.1%
other impurities—1.4%

EXAMPLE 4

Starting materials 2,6-dichlorotoluene—200 ml./h.
ammonia—99 01/h.
air—470 01/h.
nitrogen—3614 01/h.

Mole ratio

DCT:$NH_3$:$O_2$ = 1:2.5:3.5
Water circulation, fresh and waste water as in Example 1.
Yield: 72%.

Product purity 2,6-dichlorobenzonitrile—99.3%
2,6-dichlorotoluene—0.1%
water—0.1%
other impurities—0.5%

EXAMPLE 5

Starting materials as in Example 4.
water circulation—40 l./h.
fresh water—50 ml./h.
waste water—100 ml./h.
Yield: 72%

Product purity 2,6-dichlorobenzonitrile—98.8%
2,6-dichlorotoluene—0.2%
water—0.1%
other impurities—0.9%

EXAMPLE 6

Starting materials as in Example 4.

water circulation—40 l./h.
fresh water—150 ml./h.
waste water—200 ml./h.
Yield: 70%

Product purity 2,6-dichlorobenzonitrile—99.4%
2,6-dichlorotoluene—0.1%
water—0.1%
other impurities—0.4%

EXAMPLE 7

Starting materials as in Example 4.
water circulation—40 l./h.
fresh water—250 ml./h.
waste water—200 ml./h.
Yield: 68%

Product purity 2,6-dichlorobenzonitrile—99.5%
2,6-dichlorotoluene—0.1%
water—0.1%
other impurities—0.3%

EXAMPLE 8

Starting materials 2,6-dichlorotoluene (purity 99.8%)—200 ml./h.
ammonia—101 0l/h.
air—478 0l/h.
nitrogen—3604 0l/h.

Mole ratio $DCT:NH_3:O_2 = 1:2.5:3.5$
Water circulation, fresh and waste water as in Example 1.
Yield: 72%

Product purity 2,6-dichlorobenzonitrile—99.4%
2,6-dichlorotoluene—0.1%
water—0.1%
other impurities—0.4%

EXAMPLE 9

Starting materials as in Example 8
water circulation—40 l./h.
fresh water—250 ml./h.
waste water—300 ml./h.
Yield: 70%

Product purity 2,6-dichlorobenzonitrile—99.5%
2,6-dichlorotoluene—0.1%
water—0.1%
other impurities—0.3%

The product has the following sieve analysis:
<31μ—15.9%
31–125μ—18.6%
125–500μ—45.3%
500–710μ—15.5%
>710μ—4.7%

The results of the above Examples are summarised in the following Table:

| Experiment No | Starting material purity (% DCT)[1] | mole ratio $DCT:NH_3:O_2$ | fresh water (ml.) | yield (%) | product purity (% DCBN)[2] |
|---|---|---|---|---|---|
| 1 | 98.1 | 1:4:5 | 100 | 60 | 99.7 |
| 2 | 98.1 | 1:3:4 | 100 | 63 | 99.3 |
| 3 | 98.1 | 1:2:3 | 100 | 70 | 98.2 |
| 4 | 98.1 | 1:2.5:3.5 | 100 | 72 | 99.3 |
| 5 | 98.1 | 1:2.5:3.5 | 50 | 72 | 98.8 |
| 6 | 98.1 | 1:2.5:3.5 | 150 | 70 | 99.4 |
| 7 | 98.1 | 1:2.5:3.5 | 250 | 68 | 99.5 |
| 8 | 99.8 | 1:2.5:3.5 | 100 | 72 | 99.4 |
| 9 | 99.8 | 1:2.5:3.5 | 150 | 70 | 99.5 |

[1]DCT = 2,6-dichlorotoluene
[2]DCBN = 2,6-dichlorobenzonitrile

We claim:

1. In a process for the preparation of 2,6-dichlorobenzonitrile by an ammonoxidation reaction of 2,6-dichlorotoluene in a reaction mixture comprising oxygen and ammonia in the presence of a vanadium-molybdenum oxide catalyst to produce a reaction gas, and recovering the 2,6-dichlorobenzonitrile from the reaction gas, the improvement wherein the recovering step comprises spraying water into the reaction gas to cool the reaction gas and precipitate pure 2,6-dichlorobenzonitrile therefrom for recovery, while dissolving impurities.

2. The process of claim 1, wherein sufficient water is sprayed to quench the reaction gases to a temperature of from 20° to 30° C.

3. The process of claim 1, wherein water is sprayed in an amount of from 10 to 50 liters per 100 ml. of 2,6-dichlorotoluene in the reaction mixture.

4. The process of claim 3, wherein water is sprayed in an amount of from 20 to 30 liters per 100 ml. of 2,6-dichlorotoluene in the reaction mixture.

5. The process of claim 1 wherein the mole ratio of 2,6-dichlorotoluene to ammonia is 1:2 to 5.

6. The process of claim 5, wherein the mole ratio of 2,6-dichlorotoluene to ammonia is 1:2.5 to 4.

7. The process of claim 5, wherein the mole ratio of 2,6-dichlorotoluene to oxygen is 1:3 to 5.

8. The process of claim 7 wherein the reaction temperature is from 400° to 500° C.

9. The process of claim 8 wherein the contact time of the 2,6-dichlorotoluene with the catalyst is from 0.5 to 1 second.

10. The process of claim 1 carried out continuously.

11. The process of claim 1 wherein the reaction is carried out in a fluidized bed, and the water is sprayed into the reaction gas as it leaves the bed.

12. The reaction of claim 11 wherein reaction temperature is from 400° to 500° C; the contact time with the catalyst in the bed is from 0.5 to 1 second; the mole ratio of 2,6-dichlorotoluene to ammonia to oxygen is 1:2 to 5:3 to 5, and water is sprayed into the reaction gases in an amount of 10 to 50 liters per 100 ml of 2,6-dichlorotoluene in the reaction mixture.

* * * * *